(12) United States Patent
Tabacco et al.

(10) Patent No.: US 8,206,946 B2
(45) Date of Patent: Jun. 26, 2012

(54) FLUORESCENT VIRUS PROBES FOR IDENTIFICATION OF BACTERIA

(76) Inventors: Mary Beth Tabacco, Boston, MA (US); Xiaohua Qian, Sudbury, MA (US); Jaimie Russo, Chelmsford, MA (US)

( * ) Notice: Subject to any disclaimer, the term of this patent is extended or adjusted under 35 U.S.C. 154(b) by 99 days.

(21) Appl. No.: 10/393,936

(22) Filed: Mar. 24, 2003

(65) Prior Publication Data

US 2004/0191859 A1    Sep. 30, 2004

(51) Int. Cl.
*C12Q 1/68* (2006.01)
*C12P 21/06* (2006.01)
(52) U.S. Cl. .......................................... 435/69.1
(58) Field of Classification Search ............... 435/5, 7.2, 435/7.32, 29; 436/164, 172
See application file for complete search history.

(56) References Cited

U.S. PATENT DOCUMENTS

| 6,498,041 B1 * | 12/2002 | Tabacco et al. | 436/172 |
| 6,767,733 B1 * | 7/2004 | Green | 435/288.5 |
| 2001/0006783 A1 * | 7/2001 | Nogami | 435/6 |
| 2003/0022394 A1 * | 1/2003 | Dumas | 436/518 |

OTHER PUBLICATIONS

Tabacco M.B. "A New Biosensor for Rapid Identification of Bacterial Pathogens", Abstract for EPA contract No. 68D01016, National Center for Environmental Research, 2001. Available of at http://cfpub.epa.gov/ncer_abstracts/index.cfm/fuseaction/display.abstractDetail/abstract/1232.*

Tabacco, Mary Beth, Eighth Measurement and Monitoring Literature Update, The 3$^{rd}$ Harsh-Environment Mass Spectrometry Workshop, Mar. 25-28, 2002, Pasadena, California.*
Loessner, et al., "Evaluation of Luciferase Reporter Bacteriophage A511::*luxAB* for Detection of *Listeria monocytogenes* in Contaminated Foods," *Applied and Environmental Microbiology* 63(8):2961-2965 (1997).
Hennes, et al., "Fluorescently Labeled Virus Probes Show that Natural Virus Populations Can Control the Structure of Marine Microbial Communities," *Applied and Environmental Microbiology* 61(10):3623-3627 (1995).
Hennes, et al. "Direct counts of viruses in natural waters and laboratory cultures by epifluorescence microscopy," *Limmol. Ocenogr.* 40(6):1050-1055 (1995).
Goodridge, et al., "Development and Characterization of a Fluorescent-Bacteriophage Assay for Detection of *Escherichia coli* O157:H7," *Applied and Environmental Microbiology* 65(4):1397-1404 (1999).
Declaration of Mary Beth Tabacco Under 37 C.F.R. §1.132, executed May 1, 2008 (3 pgs.).
Program, The 3$^{rd}$ Harsh-Environment Mass Spectrometry Workshop and The 2$^{nd}$ NASA/JPL Miniature Vacuum Pumps Workshop, Mar. 25-28, 2002, Pasadena, CA (7 pgs.).
List of Attendees, The 3$^{rd}$ Harsh-Environment Mass Spectrometry Workshop and The 2$^{nd}$ NASA/JPL Miniature Vacuum Pumps Workshop, Mar. 25-28, 2002, Pasadena, CA (5 pgs.).

* cited by examiner

*Primary Examiner* — Robert A Zeman
(74) *Attorney, Agent, or Firm* — Casimir Jones, S.C.

(57) ABSTRACT

Bacteria in fluid systems are identified by using a fluorescently labeled virus as a molecular recognition element for bacteria. The virus, or bacteriophage, are optically encoded with fluorescent reporter molecules to allow detection and quantitation of the phage and the host/phage complex. Biosensors are provided in which the molecular recognition element is immobilized on a substrate.

15 Claims, 17 Drawing Sheets

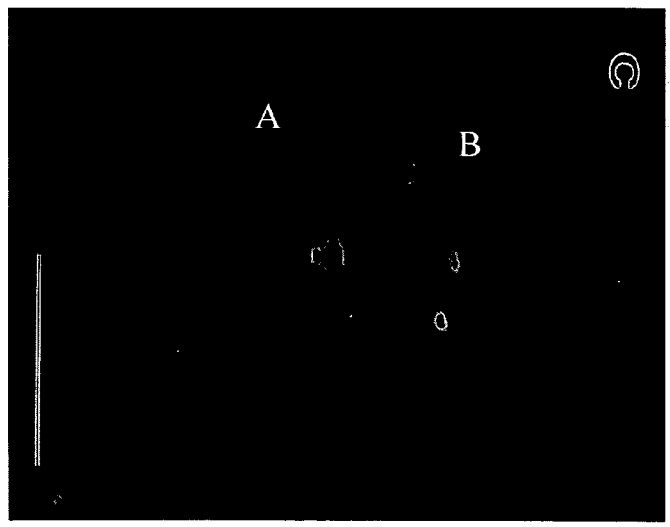

Figure 1. Two types of marine bacteria tagged with Fluorescently Labeled Virus Probes (FLVP).
From Hennes and Suttle, Appl. & Env. Micro., 61, pp3623 - 3627 (1995).

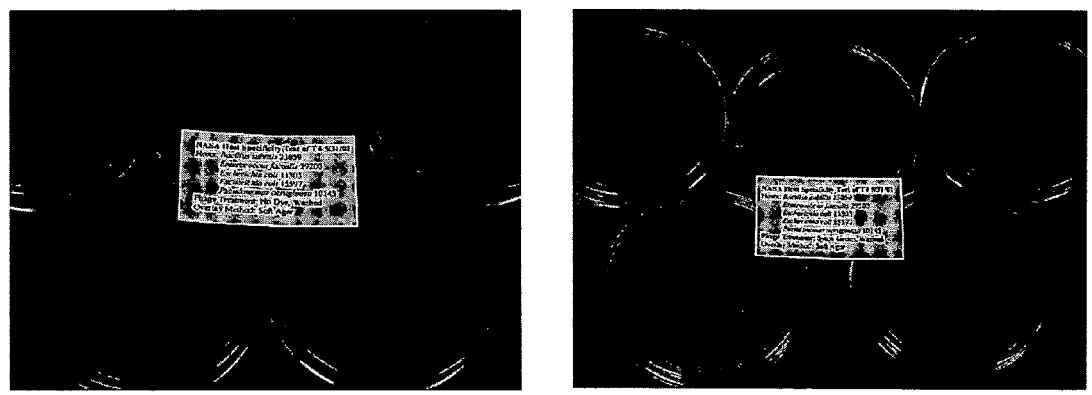

Figure 5. Agar overlay method to verify bacteriophage selectivity for host bacteria. T4 phage infects two strains of *E. coli* but does not form plaques with *P. aeruginosa*, *B. subtilis*, or *E. faecalis*. Left, plates inoculated with unlabeled T4. Right, plates inoculated with SYTOX-labeled T4.

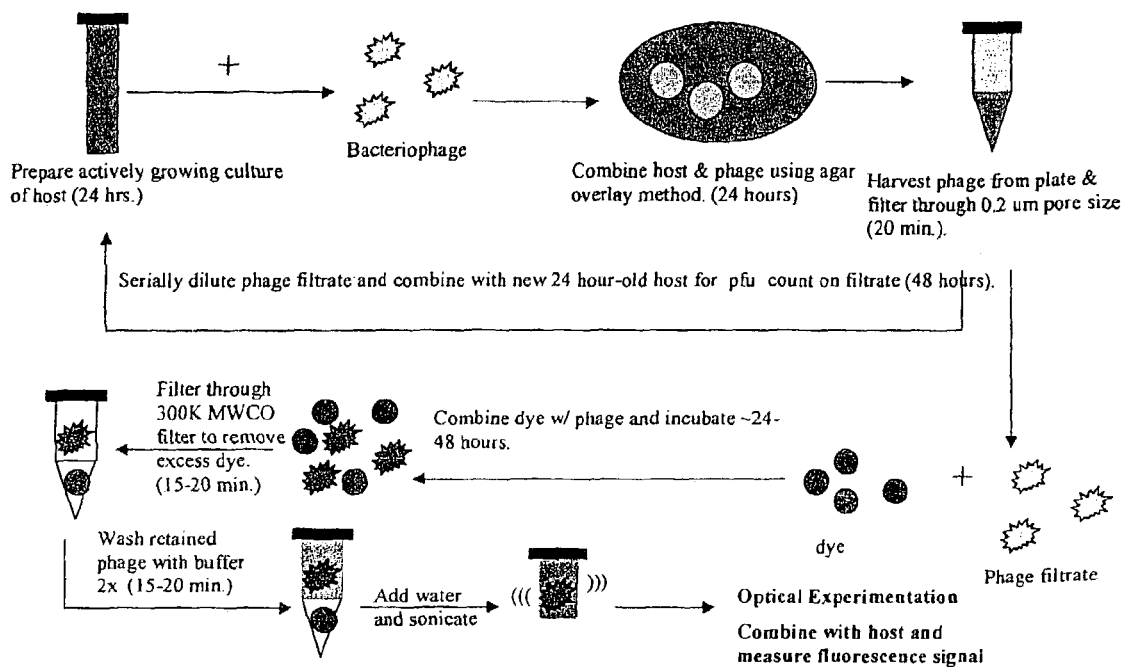
Figure 2. Preparation of FLVP's

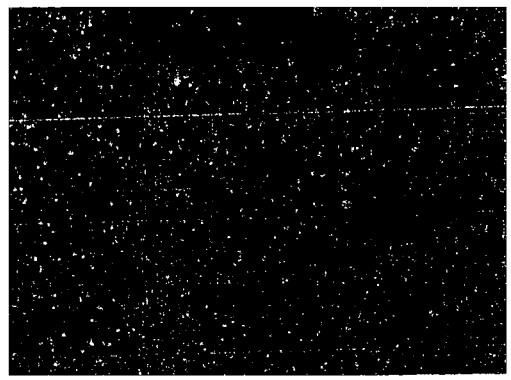
Figure 3. T4 bacteriophage stained with SYBR Green nucleic acid fluorophore.
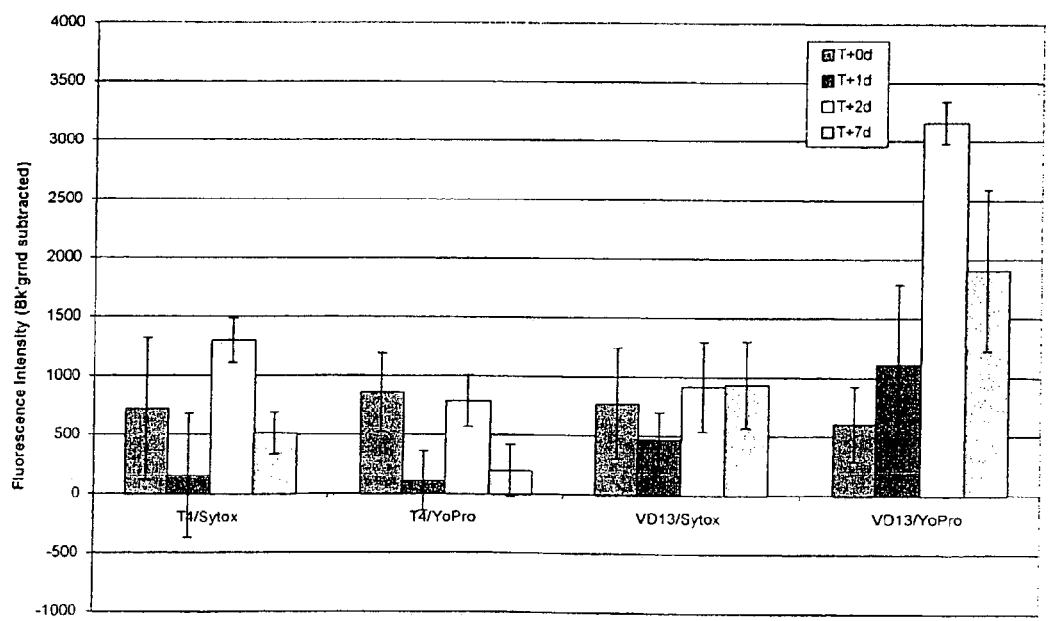

Figure 6. Testbed for Optical Characterization of FLVP's
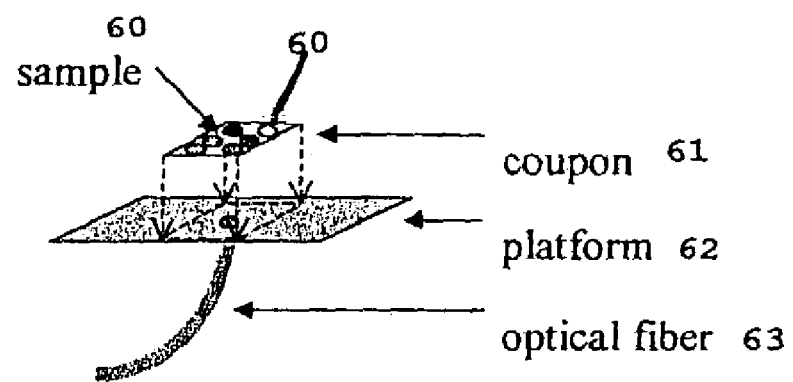

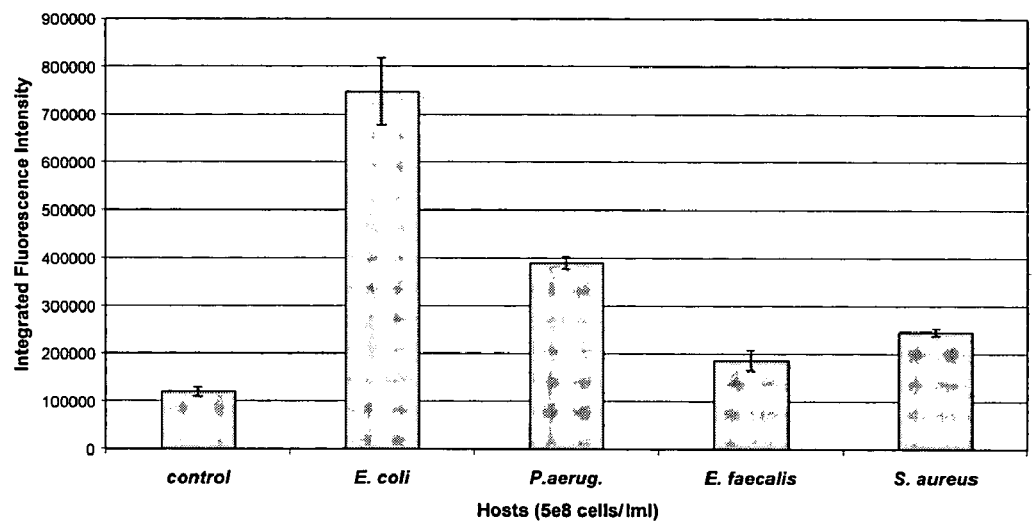
Figure 7a. MS2 FLVP/Host Selectivity
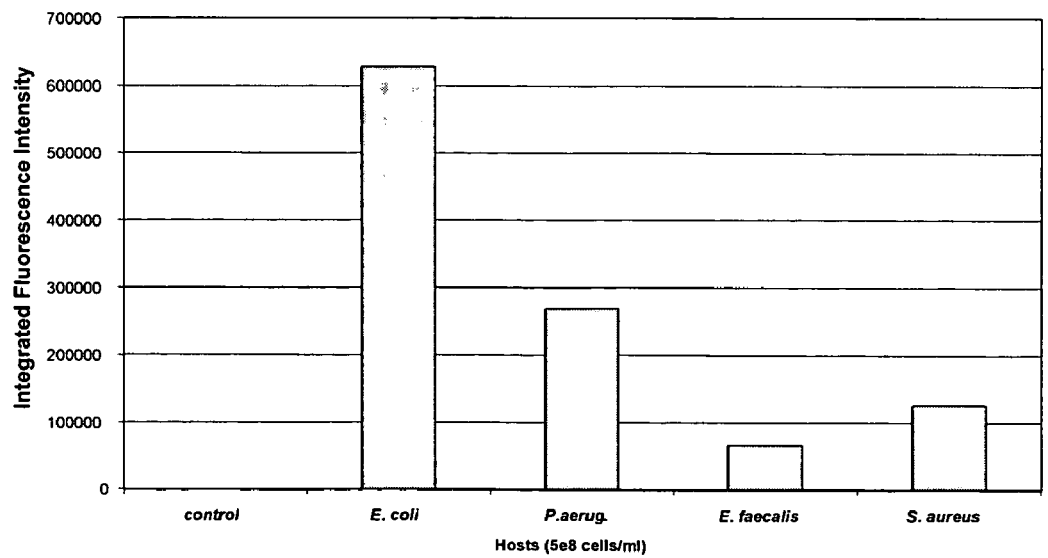
Figure 7b. MS2 FLVP/Host Selectivity
Control subtracted

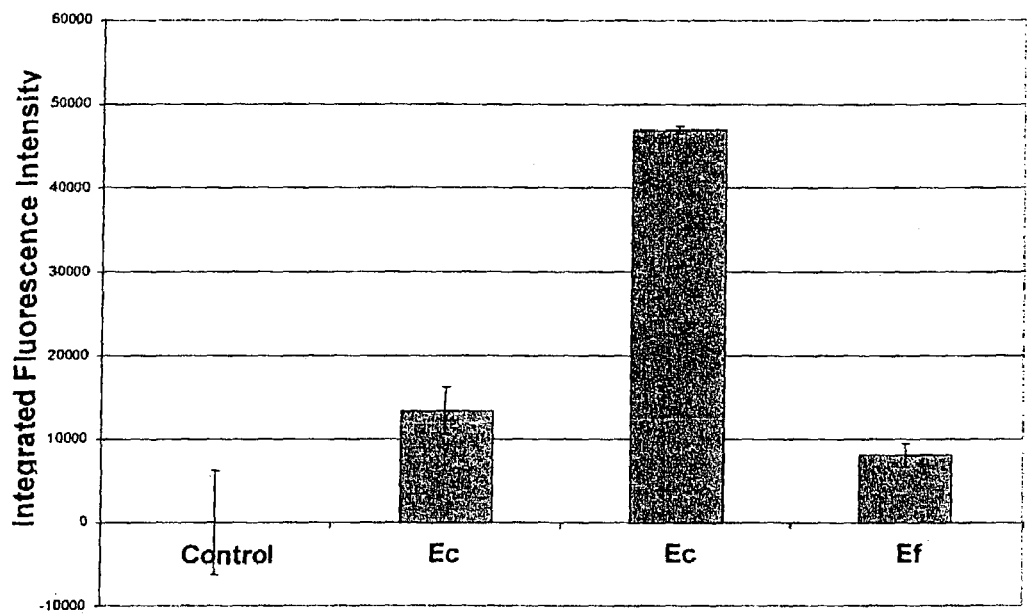
Figure 8. Reseponse of MS2/YOPRO FLVP
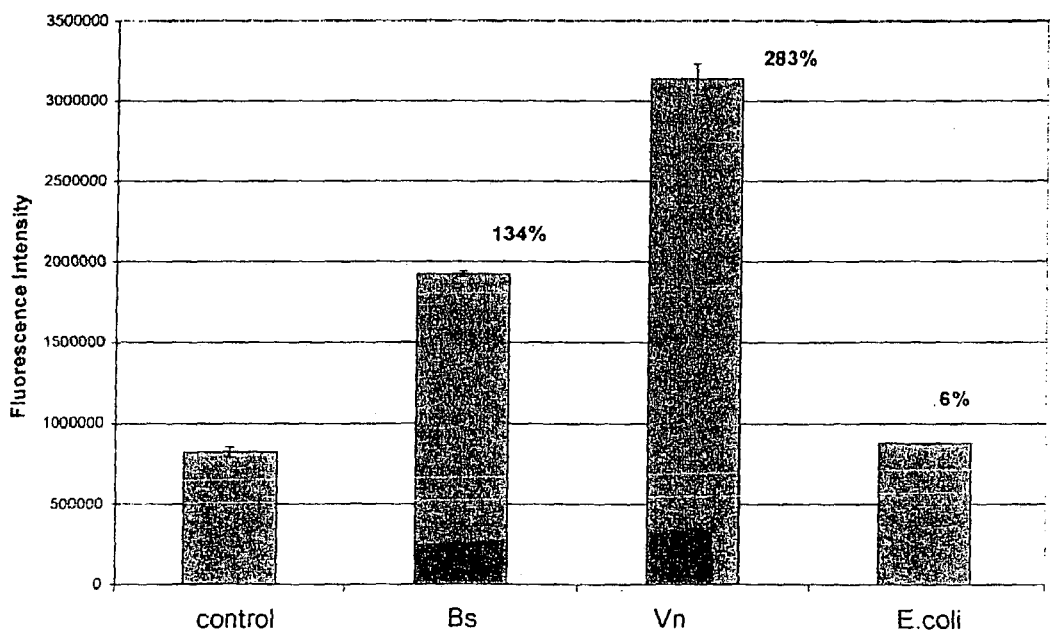
Figure 9. Response of P1 FLVP in Solution

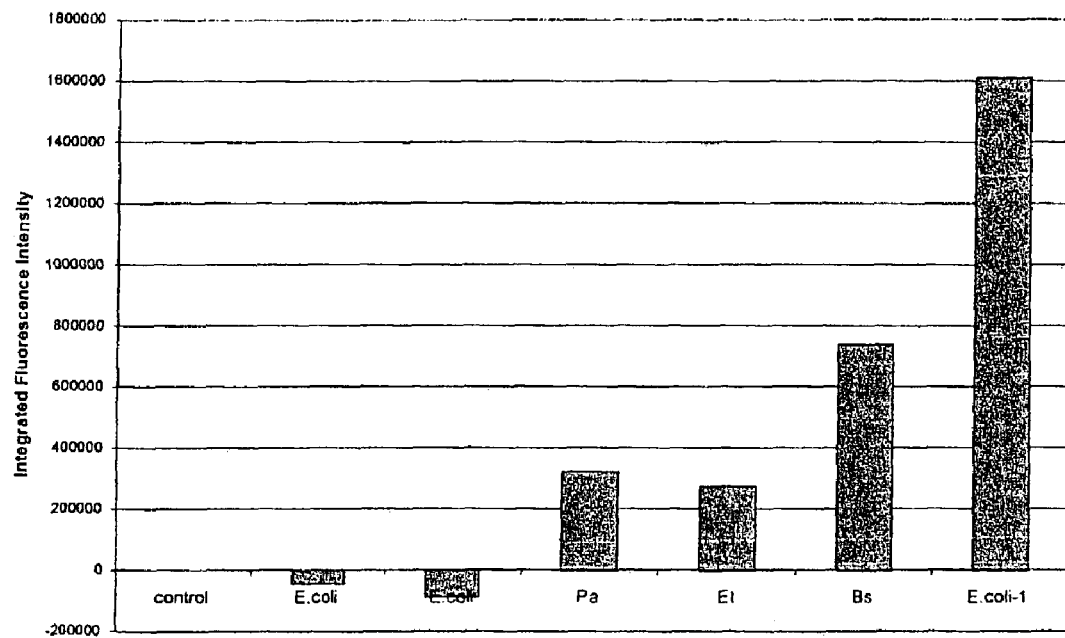
Figure 10a. T4/FLVP Specificity in Solution
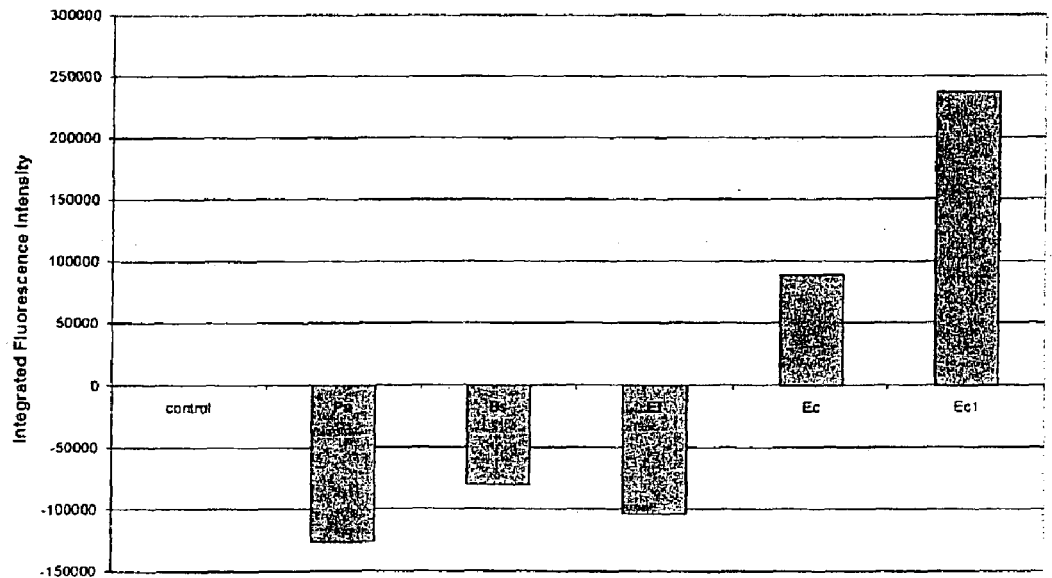
Figure 10b. T4/FLVP Specificity
Signal increase due to *Bacillus* is not observed, but staining of non-host cells is seen under the microscope.

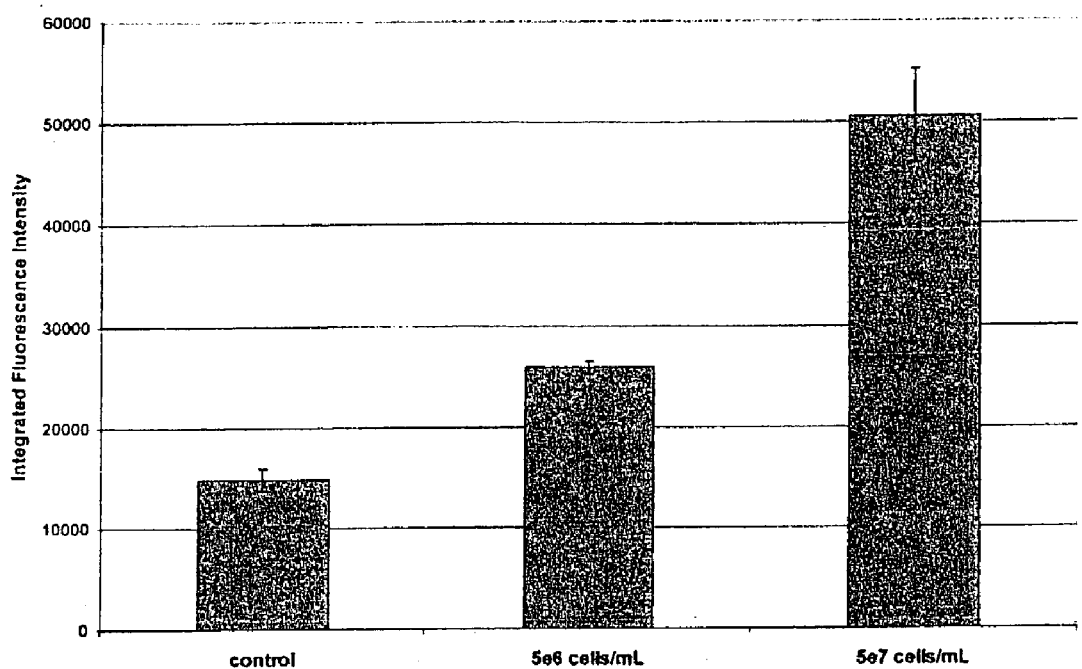
Figure 11a. P1/FLVP Response to *V. natriegens*
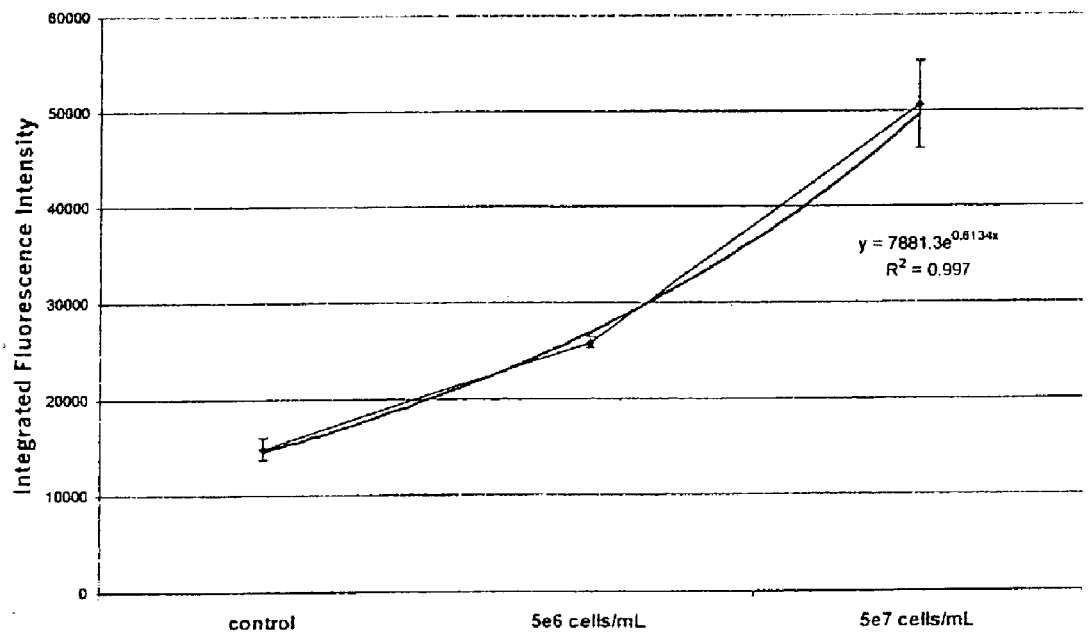
Figure 11b. Calibration Curve for P1/FLVP with *V. natriegens*

Figure 12. P1/FLVP Response to *V. natriegens*
Correcting for sample size the number of organisms in the sample ranged from 10E3 - 10E7

Figure 13. FLVP/host complexes as a function of host concentration. A – F correspond to the concentrations 10E4 – 10E8.

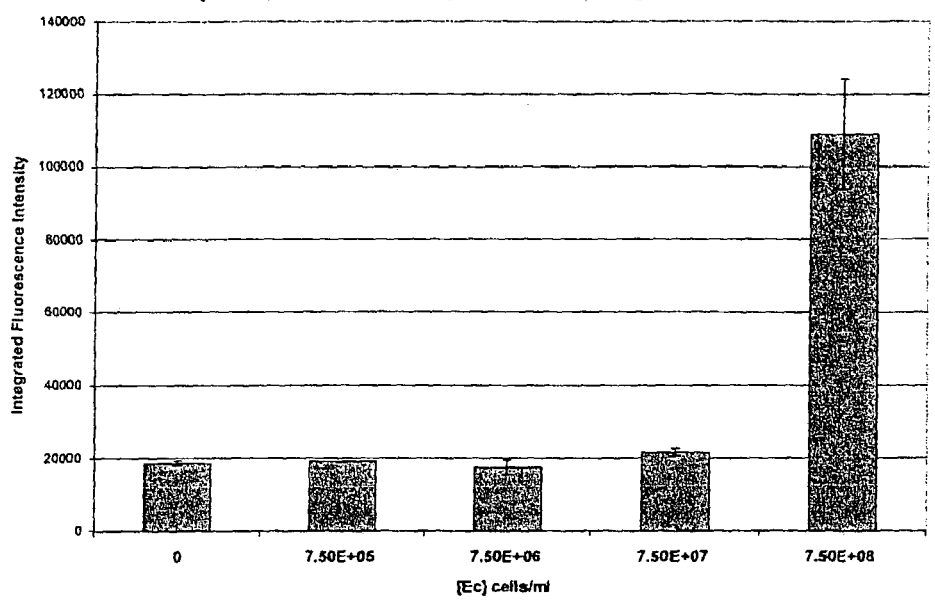

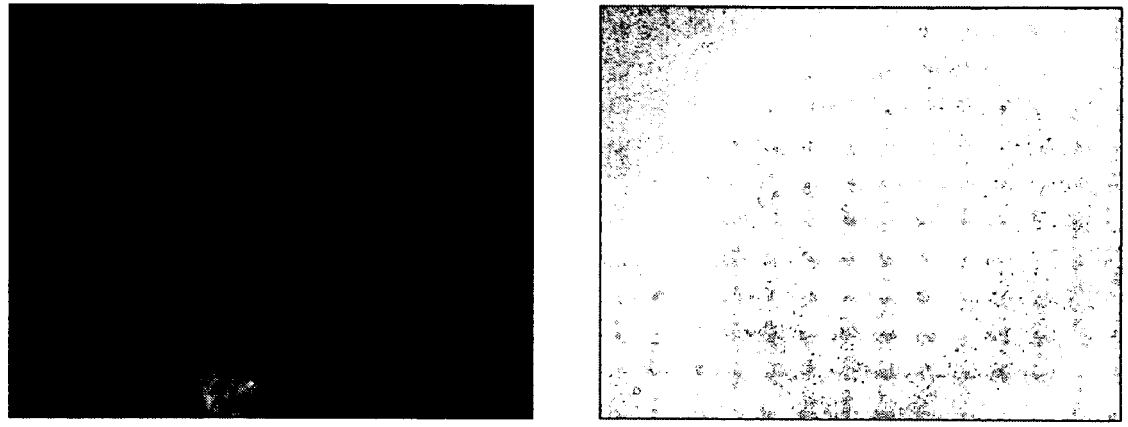
Figure 15 a&b. a.) P1/FLVP with characteristic "halo" b.) DAPI counterstain to show the bacteria host at the core of the complex.
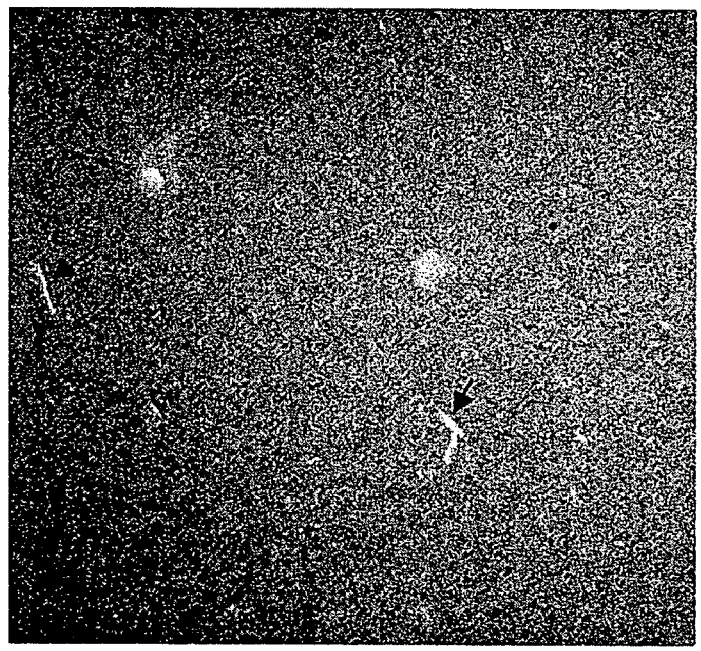
Figure 16. Representative T4/*E.coli* complex recorded using a CCD camera. Response < 1 minute.

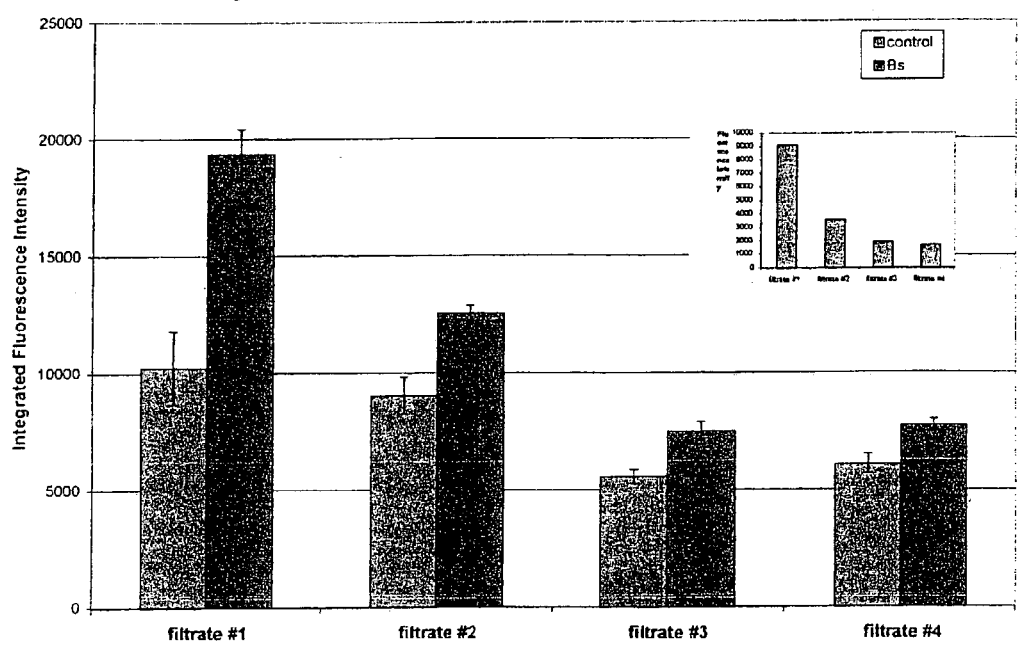
Figure 17. Response of Filtrates to *B. subtilis* (2.5e8 cell/ml)

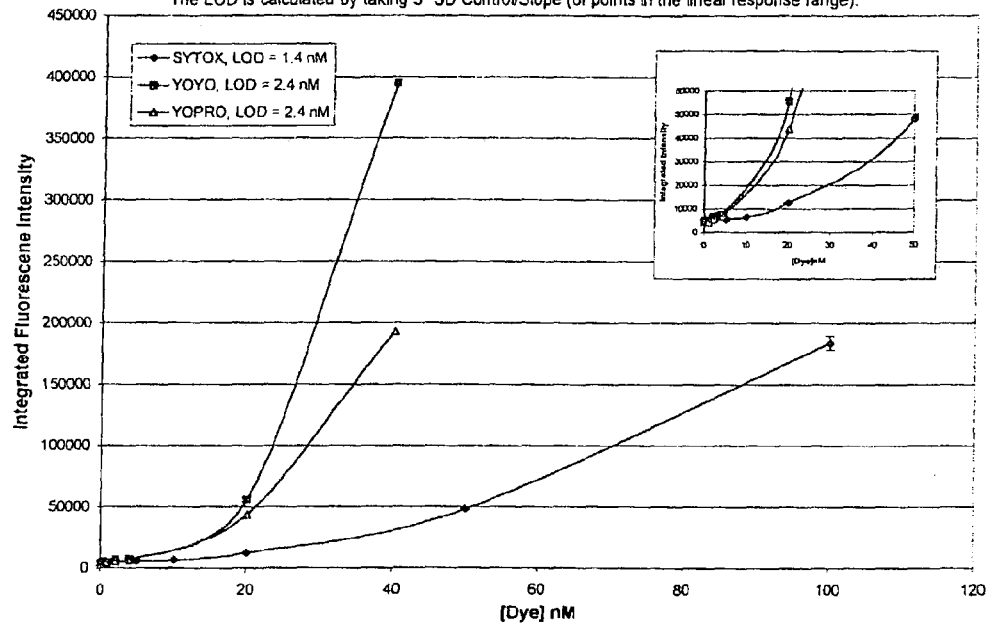
Figure 18. Calibration Curves - DNA Assay for Residual Dye
The LOD is calculated by taking 3* SD Control/Slope (of points in the linear response range).
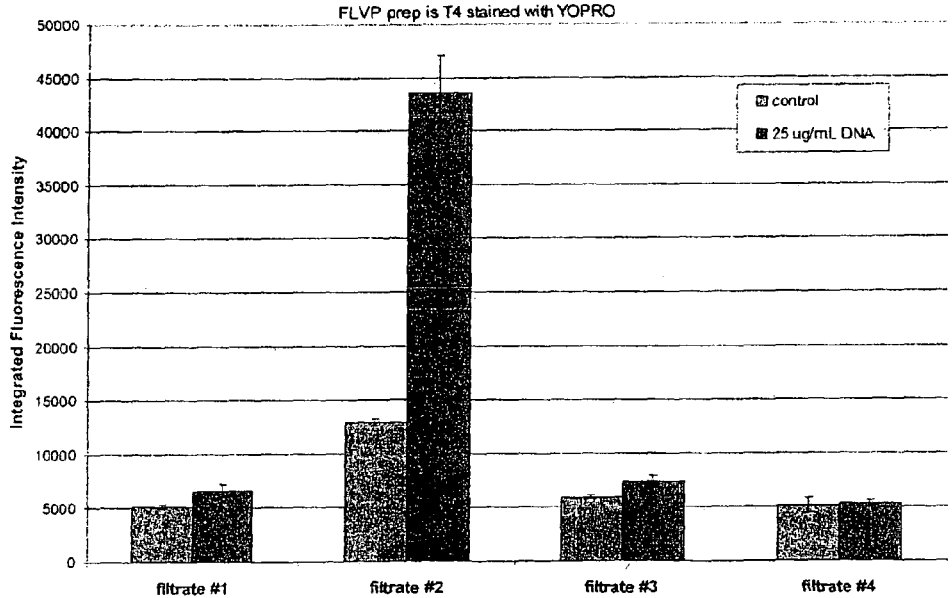
Figure 19. DNA Essay for Free Dye in Filtrates
FLVP prep is T4 stained with YOPRO

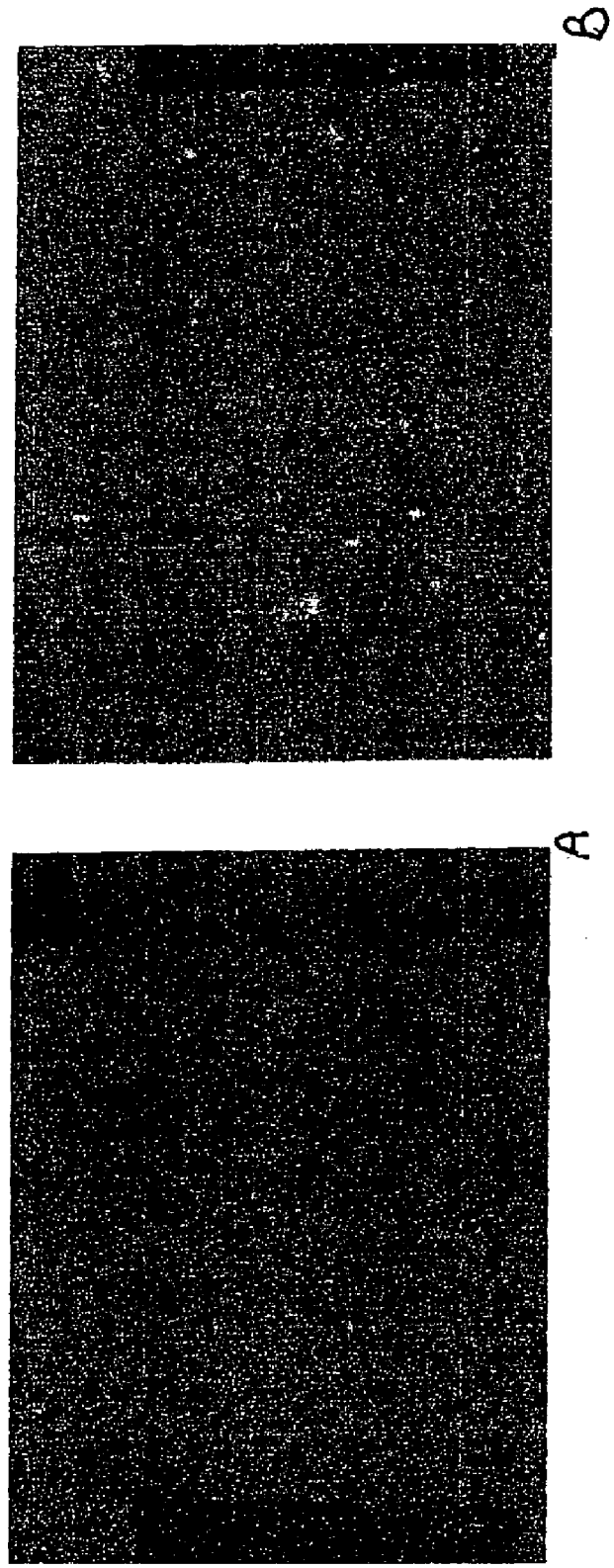
Figure 20. Left, P1 FLVP's in a mixture of non-host bacteria. Right, FLVP/cell complexes in a mixture containing host and non-host cells.

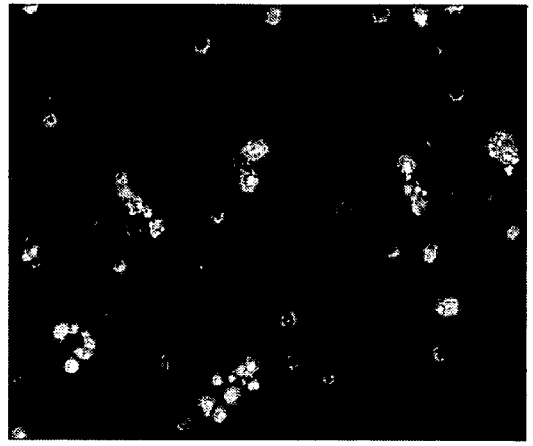
Figure 21. A FLVP biosensor for *E. coli*. T4 phage are immobilized in a PVP membrane. FLVP's can be seen in the control on the left. Phage/host complexes are seen in the photo on the right and below.
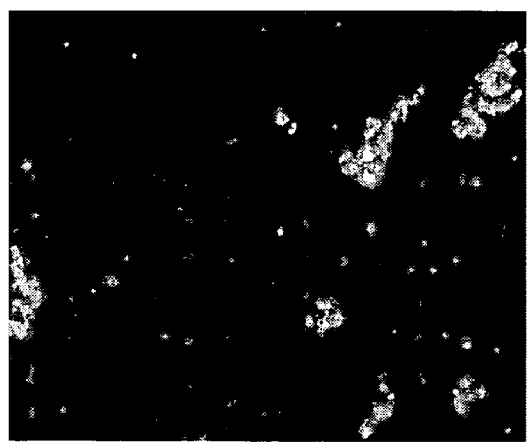

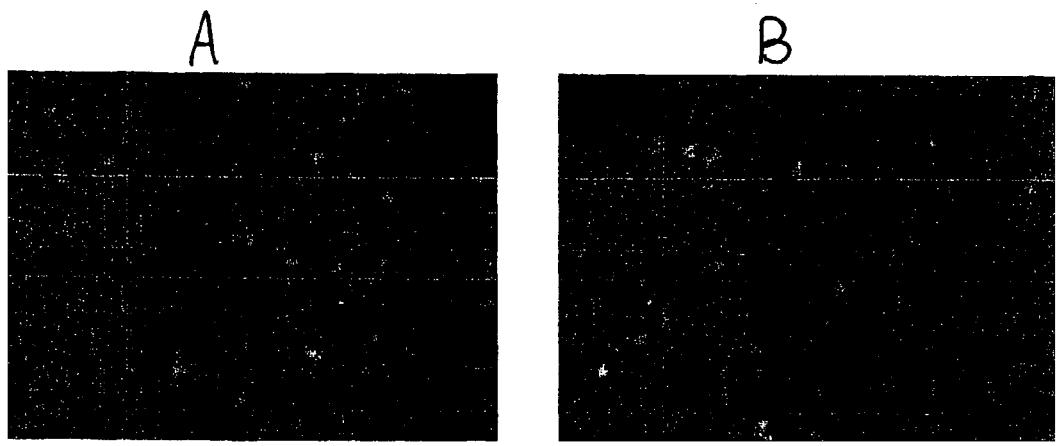
Figure 22 A P1/FLVP biosensor. Left, FLVP/host complexes on an agarose membrane; right, FLVP/host complexes on a PVP membrane.
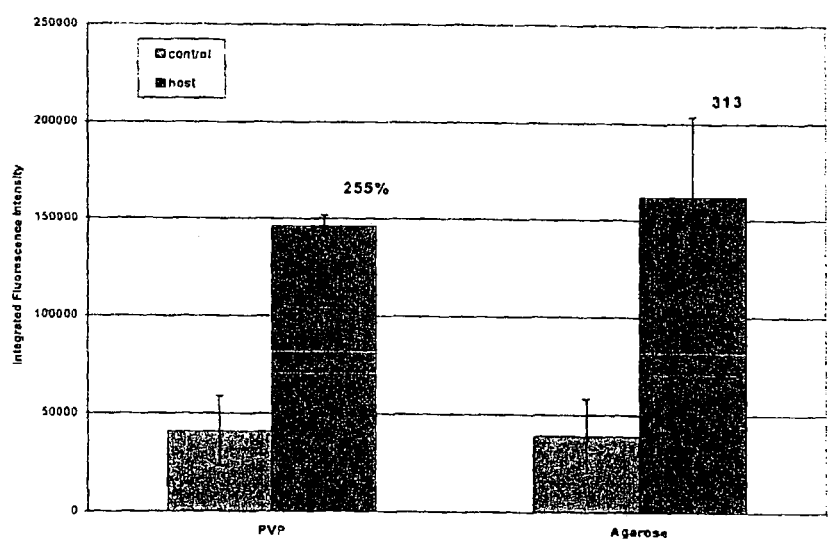

FLUORESCENT VIRUS PROBES FOR IDENTIFICATION OF BACTERIA

Research leading to the present application was conducted under Contract No. 2000-H051700-000, and the United States Government may have some rights in this invention.

FIELD OF THE INVENTION

The present invention is directed to high density, miniaturized sensor arrays for detecting a plurality of pathogens, including many species or strains of a particular pathogen to account for emerging antibiotic resistance and bioengineered bacteria.

BACKGROUND OF THE INVENTION

Presently, rapid, handheld, or portable instrumentation for determining the quality of fluids, such as natural waters, recreational waters, distributed and treated water supplies, buffers, seawater, milk, biological fluids, and gases, including air does not exist. Conventional analytical techniques, such as mass spectrometry and its variants, are currently being modified for detection and identification of microorganisms. [Holland et al., 1999; Winkler et al., 1999]. Mass spectrometry, which requires various types of sample pretreatment and/or separation, requires that large libraries of chemical signatures be generated in advance of analysis. Also, bacterial mass spectra are very irreproducible even between samples taken from the same strain. Recently, the effects of cell aging on the reproducibility of the mass spectra have been identified as a problem [Arnold et al., 1999]. Equally significant is that the instrumentation is still cumbersome and expensive, requires substantial operator expertise, and requires a large spectra reference library, making this approach unsuitable if the threat is unknown.

Polymerase chain reactors (PCR) are also being developed for detecting microorganisms, and have been recently demonstrated in a portable, if not lightweight, package [Belgrade et al., 1999]. Although very promising, the laboratory and real-time PCR-based instruments are still limited by high cost, user expertise requirements, and analysis time. Micromachined "chip" devices based on PCR, GC/MS, and flow cytometry are still laboratory curiosities. Portable Surface-enhanced Raman spectrometers are under development for detection of biological warfare agents, but they do not offer the sensitivity or specificity required for rapid detection of pathogens.

Biosensors typically incorporate a molecular receptor such as an antibody or nucleic acid fragment immobilized on a solid substrate. The transduction mechanism can be electrical, electrochemical, optical, or mass-based [Paddle, 1996]. Very elegant work has been done using antibodies and, more recently, DNA probes for detection of pathogenic microorganisms in water [Cao et al., 1995; Wadkins et al., 1998; Stahl, 1999]. Specifically in the area of food borne pathogens, immunoelectrochemical and surface-enhanced infrared sensors have been demonstrated [Brewster et al., 1996; Brown et al., 1998]. These assays, however, are inherently complex, requiring sample preparation, addition of solvents, and washing steps. Even when these steps are automated, they require the development and maintenance of fluid handling systems and reagent reservoirs, and they generate chemical waste. Additionally, producing high quality antibodies is a costly, time-consuming process, and both approaches are subject to non-specific binding. For example, several bacteria of the *Escherichia* and *Salmonella urbana* genus have been reported to cross react with antibody raised for *E. coli* O157 [Goodridge et al, 1999].

The use of aptamer technology has also been proposed for detection of pathogenic microorganisms. Aptamers are nucleic acids that have diverse functionality such as specific ligand-binding characteristics [Potyrailo et al., 1998; German et al., 1998]. Aptamers are generally synthesized using combinatorial chemistry techniques to generate very large, complex libraries of molecules ($>10^{15}$), which then must be screened, isolated, and amplified for the aptamer of interest. Hennes and Settle have demonstrated that individual viral particles (i.e., bacteriophage) can be ligated with fluorescent reporters with subsequent detection enumeration, and discrimination in a complex biological sample [Hennes et al., 1995a; Hennes et al., 1995b]. Goodridge et al. have demonstrated a similar fluorescent-bacteriophage assay in bulk solution for detecting *Escherichia coli* O157:H7 [Goodridge et al., 1999]. Viruses stained in this manner were found to adsorb to host cells with high specificity. Moreover, cells with attached fluorescently labeled viruses were clearly distinguishable from non-host cells.

SUMMARY OF THE INVENTION

It is an object of the present invention to overcome deficiencies in the prior art.

It is another object of the present invention to provide a miniaturized sensor array for detection of a plurality of pathogens.

It is a further object of the present invention to provide a detection system for many species or strains of a particular pathogen.

It is still another object of the present invention to provide a detection system including sensor redundancy to reduce the likelihood of false negatives or false positives.

There is an immediate need for rapid, portable analytical instruments to identify potentially pathogenic bacteria in fluids. This capability is required to ensure the safety of natural and manmade water supplies including source, recreational, treated, and distributed waters as mandated by the EPA, as well as the safety of fluids such as air, biological fluids, milk, and any other fluids that can be contaminated by pathogenic bacteria.

The threat arises from organisms such as *Escherichia coli*, Enterococci such as *Streptococci*, and other harmful or signature bacteria including *Bacteroides* and *Bifidabacterium*. There is historical and growing concern over the presence of pathogenic organisms in indoor air, HVAC systems, and cooling towers in commercial municipal and other public venues. Additionally, there is a great need to ensure the safety of the food supply, including but not limited to fish, meat, and other food products. Bacteria posing risks include naturally occurring bacteria such as *Legionella*, and biological warfare agents such as *Yersinia* and *Tularemia*. Further, the emergence of antibiotic-resistant or bioengineered bacteria will necessitate a detection device capable of screening for many different species of a particular pathogen.

According to the present invention, an optical sensor system is provided for detecting, identifying, and quantifying bacteria in fluids or suspensions.

The present invention provides a new type of optical biosensor that is simple, rapid, specific and sensitive. The biosensors are based on the use of Fluorescently Labeled Virus Probes (FLVP's), which are highly specific bacteriophage particles labeled with fluorescent reporters. The sensor is monitored by wavelength-specific fluorescence spectroscopy, which indicates the presence of the phage/host complex. A breadboard miniature optoelectronic interface (OEI) and data acquisition system or other type of interface can be used for reading the sensor.

Application of the FLVP technology to solid state optical sensing represents a new approach to real-time detection of bacterial pathogens. This approach eliminates the need for culturing to identify pathogens, and is an important departure from immunoassay or DNA-based sensing concepts. The miniature probes are perfectly suited for incorporation in a sensor array for simultaneous detection of many bacterial pathogens.

The optical sensors are small (0.8-5 mm), and exhibit a high degree of specificity and sensitivity for the bacterial pathogens of interest. The sensors and optical reader are ideally suited to configuration as high density multi-probe sensor arrays to screen for multiple pathogens simultaneously.

Application of the fluorescent bacteriophage technology to solid state optical sensing represents a new approach to real-time detection of bacterial pathogens and an important departure from immunoassay and DNA based sensing concepts. In addition to the desire for rapid simple analysis, the ideal bioagent signature should be immune to false negative or positive identifications and be capable of analyzing samples in a complex sample matrix. This highlights the need to make an accurate and sensitive identification of a bacterial pathogen in a complex mixture of potential interferents and other microorganisms. In actual environmental samples, the approach of the present invention has exhibited discrimination capability in a background of $10^6$ non-target bacteria with >99% accuracy for the target organism. [Hennes et al., 1995a, Hennes et al., 1995b]. Another key advantage of using bacteriophage as the detection signature is that the phage can be readily isolated and selected for the degree of specificity required. Also, the numerous optically encoded FLVP's provide inherent sensor redundancy to ensure against false negatives and false positives.

BRIEF DESCRIPTION OF THE DRAWINGS

FIG. 1 illustrates two types of marine bacteria tagged with fluorescently labeled virus probes, adapted from Hennes 1995b.

FIG. 2 is a schematic showing preparation of fluorescently labeled virus probes.

FIG. 3 shows T4 bacteriophage stained with SYBR Green I nucleic acid fluorophore.

FIG. 4 shows leaching of dyes from fluorescently labeled virus probe preparations.

FIG. 5 shows the agar overlay method to verify bacteriophage selectivity for host bacteria.

FIG. 6 shows a testbed for optical characterization of fluorescently labeled virus probes.

FIGS. 7a and 7b illustrate MS2 FLVP/host selectivity. FIG. 7a includes the control. FIG. 7b has had the control subtracted.

FIG. 8 shows the response of MS2/YOPRO fluorescently labeled virus probe.

FIG. 9 shows the response of P1/fluorescently labeled virus probe in solution.

FIGS. 10a and 10b show T4 fluorescently labeled virus probe specificity in solution. In FIG. 10b, the signal increase due to *Bacillus* was not observed.

FIG. 11a shows P1/fluorescently labeled virus probe, response to *V. natriegens*.

FIG. 11b shows a calibration curve for P1/fluorescently labeled virus probe. with *V. natriegens.*

FIG. 12 shows P1/fluorescently labeled virus probe, response to *V. natriegens*.

FIGS. 13a-13f show fluorescently labeled virus probe, host complexes as a function of host concentrations. FIGS. 13a-13f correspond to the concentrations shown in FIGS. 10E4-10E8.

FIG. 14 illustrates the P1/fluorescently labeled virus probe, response to *E. coli.*

FIG. 15a shows P1/fluorescently labeled virus probe, with a characteristic "halo" of phage around the host, *Vibrio naltriegens.*

FIG. 15b shows a DAPI counterstain to show the bacteria host at the core of the complex.

FIG. 16 shows representative T4 *E. coil* complex recorded in real time using a CCD camera.

FIG. 17 shows the response of filtrates to *B. subtilis.*

FIG. 18 is calibration curves for DNA assay for residual dye.

FIG. 19 shows the results of a DNA assay for free dye in filtrates.

FIG. 20a shows P1/fluorescently labeled virus probe, in a mixture of non-host bacteria.

FIG. 20b shows fluorescently labeled virus probe cell complexes in a mixture containing host and non-host cells.

FIGS. 21a-c show a fluorescently labeled virus probe biosensor for *E. coli*, in which T4 phage were stained with YOPRO or SYTOX and immobilized in a PVP polymer membrane. FIG. 21a shows control. Phage/host complexes are seen in FIGS. 21b and 21c.

FIGS. 22a and b show a P1/fluorescently labeled virus probe, biosensor. FIG. 22a shows fluorescently labeled virus probe/host complexes on an agarose membrane. FIG. 22b shows fluorescently labeled virus probe/host complexes on a PVP membrane.

FIG. 23 shows the response of FLVP biosensors prepared on PVP or agarose membranes to host bacteria, *Vibrio natriegens.*

DETAILED DESCRIPTION OF THE INVENTION

In the present invention, fluorescently labeled virus probes (FLVP's) are used for selective and sensitive detection of bacterial pathogens. These bacterial pathogens can be from any source, and can include waterborne, airborne, aerosolized (indoor/outdoor), foodborne, and extraterrestrial as well as bioengineered pathogens. This approach avoids the problems associated with antibody-based biosensors and nucleic acid (DNA) probes including non-specific binding and unreliable sensitivity. The sensors are uniquely versatile in that they can be configured to detect many species of a particular genus, or a single species, by using an ensemble of bacteriophage, and will also be rapid, sensitive and simple. The recent advances in the development of highly fluorescent reporter molecules for use in cell and molecular biology have been found to make them particularly useful in optical sensing. The present invention uses fluorescent reporter molecules and molecular recognition elements to develop semi-selective sensors to detect broad classes of microorganisms that pose human health and biological warfare threats. For example, in one type of bacterial sensor fluorescent reporters are immobilized in a biopolymer membrane on an optical waveguide to form the sensor surface. When the microorganism adheres to the surface the fluorophore, which can be a DNA/RNA stain, is diffuses through the cell membrane and intercalates into the bacterial nucleic acid, causing a change in the fluorescent signal.

Hennes and Suttle have demonstrated that individual viral particles (i.e., bacteriophage) can be ligated with similar fluorescent reporters with subsequent detection, enumeration and discrimination in a complex biological sample [Hennes et al., 1995a; Hennes et al., 1995b]. A similar Fluorescent-Bacteriophage Assay has recently been demonstrated in bulk solution for detection of *Escherichia coli* 0157:H7. [Goodridge et al., 1999]. Viruses stained in this manner were found to adsorb to host cells with high specificity. Moreover, cells with attached FLV's were clearly distinguishable from non-host cells as shown in FIG. 1.

The approach of the present invention is based on the use of these fluorescently labeled viruses, with well-defined host ranges, to tag and identify the target pathogen in a mixed microbial community.

FLVP technology applied to optical sensing has a number of advantages over existing and developmental methods for detecting bacterial pathogens as summarized below:
1. Speed: adsorption of FLVP's to target cells takes place within seconds or minutes.
2. Sensitivity: using FLVPs it is possible to quantify the abundance of even a few cells per milliliter.
3. Specificity: binding of non-target bacteria was undetectable against a natural biological background of >$10^6$ bacteria/ml. When host cells were added to natural seawater they were quantified using the FLVP approach with 99%+/−2% efficiency. This feature is particularly important for the present application where false negatives are not acceptable, and false positives would potentially result in greater cost and logistical complications.
4. Multi-analyte sensing: by encoding different bacteriophage with fluorochromes that fluoresce at different wavelengths it is possible to quantify the abundance of a number of different pathogens in the same sample.
5. Simplicity: bacteriophage are easily isolated in large numbers from host cells; pathogens can be detected and quantified without the need for culturing, thereby minimizing use of reagents and requiring minimal manning or expertise. The sensors can be configured as a probe or "swab". Alternatively, very low volume samples can be introduced, using microfluidic components if needed.
6. Cost: bacteriophage are relatively easy to isolate and inexpensive to purify compared to monoclonal antibodies and aptamers [13, 16].

The optically encoded phage for specific target pathogens can be configured in a miniaturized sensor array to build a multi-pathogen detection system. This affords simultaneous detection of many species or stains of a particular pathogen, to account for emerging antibiotic resistance, and sensor redundancy to reduce the likelihood of false negatives or positives.

The bacteriophage was labeled with a broad spectrum of fluorescent probes to provide wavelength flexibility and encoding diversity when considering multi-sensor arrays. It was demonstrated that the bacteriophage retained their host specificity after labeling. The virus probes were immobilized on optical substrates, such as optical waveguides glass, sol-gels, and polymer films, and retained their ability to interact with the bacteria of interest. The response time of the solid phase bacteriophage assay was extremely rapid, particularly when compared with conventional assays.

These features, combined with the ability to fabricate high density, miniaturized sensor arrays using optical waveguides or biosensor chips, and array detection, form the basis for the multi-pathogen detection system of the present invention. This capability further enables the detection of many species or strains of a particular pathogen (to account for emerging antibiotic resistance) and sensor redundancy to further reduce the likelihood of false negatives or positives.

Preparation of Fluorescent Virus Probes

The fluorescently labeled virus probes (also refereed to as FLVP's or FLV-probes), are prepared using a modification of the technique described by Hennes et al. [Hennes et al. 1995a, Hennes et al. 1995b]. This technique is shown schematically in FIG. 2. The upper half of FIG. 2 represents propagation and quantitation of the phage, and the lower half of FIG. 2 follows the process of staining, purifying, and testing the FLV probes. This procedure is summarized as follows:
1. Prepare a 1 ml sample of 0.2 micron filtered phage to ~$1\times10^{11}$ pfu/ml.
2. Incubate the phage with 5 μM fluorophore for 48 to 72 hours at 4° C. in the dark.
3. Add 500 μl of phage to each of two pre-washed Microcon YM-50 centrifugal filter devices (50,000 MWCO) (Millipore) and filter.
4. Discard the filtrate and re-suspend the phage in 500 μL distilled water or growth media in fresh prewashed Microcon YM-50 devices.
5. Wash FLPV samples three times with distilled water or growth media.
6. Re-suspend the FLVP in 500 μl distilled water or growth media.
7. Prepare suspensions of the bacterial samples (host and non-target) in water to ~$5\times10^8$ cells/ml; e.g., *E. coli, E. faecalis, P. aeruginosa, S. aureus, B. subtilis,* and *Acinetobacter* sp.
8. Pipette 10 μl aliquots of FLVP suspension onto seven different glass substrates, three replicates each, followed by adding 10 μl each of the six different bacterial suspensions, including a control with water.
9. Allow ten minutes for incubation in the dark.
10. Measure fluorescence signal using Acton system. Confirm FLVP/host complex using an epi-fluorescence microscope and record with digital camera.

A summary of the fluorophores and phage combinations that were tested as described above is shown in Table 1. Each of the fluorophores is a nucleic acid stain. Some of these dyes stain both DNA and RNA viruses, although a fluorophore such as YOPRO exhibits a preference for staining DNA. All of these fluorophores are based on the cyanine family of dyes.

TABLE 1

Phage and Fluorophores Used to Prepare FLVP's

| | Fluorophore | | | | |
|---|---|---|---|---|---|
| Phage | SYTOX | YOPRO | YOYO | SYBR-Gr | POPO |
| MS2 | ++ | + | ++ | ++/− | |
| T4 | ++ | + | + | ++/− | ++ |
| VD13 | ++ | + | + | | |
| P1 | ++ | + | | ++/− | |

++ strong fluorescence
+ moderate fluorescence
− weak staining or photobleaching Many types of conventional dyes can be used in the present invention, including nucleic acid strains (i.e., DNA and RNA stains), protein stains such as Eosin Y, membrane strains such as lipophilic rhodamines and fluoresceins. One skilled in the art can readily determine which dyes can be used because they can stain nucleic acids or proteins. This determination can be effected without undue experimentation.

In selecting a fluorophore for use in detecting a particular bacterium, one could rely upon fluorophore binding constants. However, these constants are not available for all dyes, and not specifically for dye/virus interactions.

Fluorophores are currently selected primarily from the general family of nucleic acid stains (e.g., DNA-single stranded; DNA-double stranded; RNA; protein stains; membrane stains). Down selection is largely empirically based on binding constants where available, absence of dye leaching from the virus, high fluorescence quantum yield, observation of change in fluorescence property upon interaction with target bacteria. These are all relatively straightforward methods for choosing an appropriate fluorophore, and can readily be accomplished by one skilled in the art without undue experimentation.

Direct Enumeration Using Fluorescence Microscopy

Visualization and direct counting of fluorescently labeled virus probes provides a rapid alternative to traditional plaque counts. The direct counts should be somewhat higher than the plaque counts because all stained phage will be counted, even if they have lost the ability to infect the host. Direct counts can be done for fluorescently labeled virus probes prepared by incubating phage with 10 µM SYTOX or YOPRO for about 48 hours. A second method is a rapid stain with SYBR Green dye with an added antifading reagent. FIG. 3 shows an example of T4 phage (*E. coli*) stained with SYBR Green I fluorophore. Fluorescently labeled virus probes made with T4 and VD13 (*E. faecalis*) were also counted before and after successive washing steps to remove residual dye from the fluorescently labeled virus probe preparation procedure. No significant loss of fluorescently labeled virus probe was observed after washing. A rapid stain method using SYBR Green I and II was tested with MS2 phage (*E. coli*), with the latter giving somewhat better resolution with the unaided eye. Samples were sent to a university colleague for independent counting, and the direct count obtained in this experiment agreed with the colleague's count within 30%.

Preliminary Studies of Phage Stability

Preparation of fluorescently labeled virus probes generally requires several days. In an effort to reduce the preparation time required, the lifetime and stability of the phage were studied. Phage concentrations were measured using either plaque counts (plating) or direct count (staining and fluorescence microscope counting) for phage as both harvested (unwashed) and washed samples. The results are summarized in Table 2. These results indicate that most of the phage are still viable and can be stored for periods of at least four weeks.

TABLE 2

Phase Storage Stability

| Fresh | T4 as harvested | T4 washed |
|---|---|---|
| Direct phage/ml | $1.0 \times 10^{10}$ | |
| Plaque pfu/ml | $3.7 \times 10^{9}$ | |
| 24 hours | | |
| Direct phage/ml | | $4.3 \times 10^{9}$ |
| Plaque pfu/ml | | $3.3 \times 10^{9}$ |
| 120 hours | | |
| Direct phage/ml | $7.5 \times 10^{9}$ | $3.4 \times 10^{9}$ |
| Plaque pfu/ml | | |
| 2 weeks | | |
| Plaque pfu/ml | $1.7 \times 10^{9}$ | $8.5 \times 10^{9}$ |

Stability of the Fluorescently Labeled Virus Probes and Dye Leaching

This experiment was designed to measure any leakage of the dye from the virus probe after labeling with fluorophore. If fluorophore leaches from the fluorescently labeled virus probe, this would result in free dye in solution, which would itself stain both host and non-host bacteria. Fluorescently labeled virus probes of T4 and VD13 stained with both SYTOX and YOPRO were prepared. 100 µl of fluorescently labeled virus probe preparation was aliquoted to each of five vials. The samples were stored for seven days. At 24 hours, 48 hours, and after seven days, the fluorescently labeled virus probe preparations were sampled and analyzed for fluorescence signal. The fluorescence intensity arising from any leached dye was "amplified" by titrating with DNA (nucleic acid fluorophores whose quantum yield increases upon binding nucleic acid). After incubation, triplicate samples were taken from each vial and the fluorescence emission was analyzed using a double monochromator system. As shown in FIG. 4, the signals do not change much over time and are well below typical fluorescence signals from phage/host complexes. This suggests that there is little detectable free dye and good binding between the fluorophores and the phage. The increase in signal for VD13 with YOPRO suggests that YOPRO may have a lower affinity for VD13 than does SYTOX.

Testing Specificity and Discrimination Capability

Four stages were used for testing and confirming the selectivity of the bacteriophage for their host bacteria:
1. Phage (unlabeled) ability to form plaques with host and non-host bacteria using agar overlay method.
2. Fluorescently labeled virus probe ability to form plaques with host and non-host bacteria using agar overlay method.
3. Fluorescently labeled virus probe selectivity in solution phase studies using host and non-host bacteria.
4. Fluorescently labeled virus probe selectivity when immobilized in a solid state sensing film.

In the first stage, Phase I, bacteriophage/host pairs were selected based on commercial availability, and obtained from the American Type Culture Collection (ATCC). Selectivity of the phage for its host was checked using soft or hard agar overlay methods as outlined by the ATCC. The presence of plaques (clearing) on the plates indicates that the phage has infected the bacteria. Non-host bacteria were inoculated with phage to verify the absence of non-host interaction. An example of these results is shown in FIG. 5, which shows five culture plates with bacterial lawns, each of which was inoculated with T4. The bacteria are two strains of *E. coli*, *P. aeruglnosa*, *B. subtilis*, and *E. faecalis*. FIG. 5a shows very similar plaque formation by SYTOX-labeled T4 with the *E. coli*, but no plaque formation with the non-host bacteria. Tables 3a and 3b summarize the specificity studies using a conventional agar overlay method, with Table 3a showing unlabeled bacteriophage and Table 3b showing fluorescently labeled bacteriophage.

TABLE 3a

Host Specificity Using Unlabeled Bacteriophage*

| Bacterial Host | MS2 | T4 | VD13 | P1 |
|---|---|---|---|---|
| *E. coli* (ATCC#15597) | + | +'** | | |
| *E. Coli* (ATCC#11303) | | + | | |
| *E. herbicola* (ATCC#33242) | — | | | |
| *B. subtilis* (ATCC#6633, #23059) | — | — | — | — |
| *P. aeruginosa* (ATCC#10145) | — | — | — | — |

TABLE 3a-continued

Host Specificity Using Unlabeled Bacteriophage*

| Bacterial Host | MS2 | T4 | VD13 | P1 |
|---|---|---|---|---|
| *Acinetobacter* sp. | — | | | |
| *E. faecalis* (ATCC#29200) | | | + | |
| *Vibrio natriegens* | | | | + |

*The absence of +/− means that the bacteria was not part of the challenge set.
**ATCC reports T4 selective for *E. coli*#11303; some cross reactivity on the plates was observed.

TABLE 3b

Host Specificity Using Fluorescently Labeled Bacteriophage

| Bacterial Host | MS2 | T4 | VD13 | P1 |
|---|---|---|---|---|
| *E. coli* (ATCC#15597) | + | +'** | — | |
| *E. Coli* (ATCC#11303) | + | + | — | — |
| *E. herbicola* (ATCC#33242) | | | | |
| *B. subtilis* (ATCC# 6633, #23059) | — | — | — | — |
| *P. aeruginosa* (ATCC#10145) | — | — | — | — |
| *Acinetobacter* sp. | | | | |
| *E. faecalis* (ATCC#29200) | — | | + | — |
| *Vibrio natriegens* | | | | + |

*The absence of +/− means that the bacteria was not part of the challenge set.
**ATCC reports T4 selective for *E. coli*#11303; some cross reactivity on the plates was observed.

Test of Phage Lysogeny

The agar overlay results shown in FIG. 5 provide only binary information indicating that there are phage present capable of selective infection of the host bacteria. The plaque forming ability of stained (i.e., fluorescently labeled virus probe) and unstained phage were tested using VD13. The fluorescently labeled virus probe samples were stained with SYTOX and the other with YOPRO nucleic acid fluorophores. After serial dilution and plating, plaque counts were done for all samples. These results are summarized in Table 4. Unstained VD13 gave a count of $6.0 \times 10^8$ pfu/ml. The SYTOX and YOPRO samples gave counts of $4.5 \times 10^4$ pfu/ml and $3.6 \times 10^6$ pfu/ml, respectively. The results with T4 were less dramatic, but the plaque forming unit counts were reduced somewhat after staining.

TABLE 4

Test of Phage Lysogeny

| | VD13 | T4 |
|---|---|---|
| Unstained | $6.8 \times 10^8$ | $1.5 \times 10^7$ |
| SYTOX | $4.5 \times 10^4$ | $7.8 \times 10^6$ |
| YOPRO | $3.6 \times 10^6$ | $1.3 \times 10^7$ |

Other work conducted with the SP10 phage for *Bacillus subtilis* suggested that the phage, once stained (to become a fluorescently labeled virus probe) have a compromised ability to infect their host. This is reflected in lower plaque counts. This may be due to the nature of the fluorophore interaction with the phage. Typically, the nucleic acid fluorophores interact with nucleic acid by intercalating or otherwise crosslinking the DNA. The plaques that are formed with the fluorescently labeled virus probe samples could arise from unstained or weakly stained phage, which are also present in the sample.

Fluorescence Measurements and Epi-Fluorescence Microscopy Studies

Fluorescence measurements of the fluorescently labeled virus probes/host complex were made using a double monochromator system with fiber optic interface as shown in FIG. 6. In addition to a double monochromator system for measuring fluorescence of the fluorescently labeled virus probes/host complex, other types of measuring systems can be used. Some of these types of measuring systems include CCD and other array based detection systems; fluorescence and other microscope imaging; fluorescence excitation (absorption) and emission; fluorescence lifetime. For simultaneous multi-pathogen detection, multiplexing and wavelength discrimination are preferred systems. Other conventional systems that can be used include miniature spectrometers, spectrometers and a card/chip, or custom detection systems based upon fluorometry. The monochromators provide wavelength tunable light for exciting the fluorescently labeled virus probes host complex and wavelength specific detection using a photomuitiplier tube. Excitation light is coupled to the sensor using a fiber optic. Samples are placed on an optical window 61 in a 2×3 array of microdroplets, typically ranging in size from about 10 to 100 μl. This window is placed onto a platform 62 connected to an optical fiber 63. The fluorescence emission is returned over the same optical fiber 63 and detected. The samples were also examined after an experiment using a Nikon epi-fluorescence microscope. These images were captured digitally using a Nikon Cool Pix camera attachment to provide visual confirmation of the fluorescently labeled virus probes' interaction with the target cells.

Solution phase experiments were performed with fluorescently labeled virus probes prepared from four different bacteriophages: MS2 and T4 (*E. coli*), VD13 (*E. faecalis*), and P1 (*Vibria natriegens*). Initial fluorescently labeled virus probe/host selectivity studies in solution were conducted using the MS2/fluorescently labeled virus probe with *E. coli* host and non-host organisms.

The experimental procedure involved preparing a 1:1 (volume) mixture of the fluorescently labeled virus probes with each of the challenged bacteria. The mixture was incubated for about 10 to about 30 minutes, depending upon the experiment. Changes in the fluorescence intensity between the fluorescently labeled virus probe solution alone, and the fluorescently labeled virus probe plus bacteria, were monitored over a narrow band of wavelengths corresponding to the peak emission wavelength of the fluorescent reporter. FIGS. 7a and 7b show some of these results. In FIG. 7a, 1e9 pfu/ml phage MS2 were stained for 48 hours with 5 μM SYTOX dye. Fluorescently labeled virus probes were combined in 1:1 ratio with 5e8 cells/ml of each bacterium, and allowed to incubate at room temperature for 15 minutes. Measurements were taken on an Acton system with three 10 μl droplets of sample per slide. In FIG. 7a, the integrated fluorescence intensity from the MS2/bacteria complex was plated for each bacterial type. The control is a sample of the MS2/fluorescently labeled virus probe plus water. It should be noted that, because the phage are fluorescently labeled, they contribute to the background signal.

FIG. 7b shows fluorescently labeled virus probes/host selectivity with the control subtracted. These results show good selectivity for the *E. coli* host. The degree of apparent cross-reactivity with *Pseudomonas* and *Staphylococcus* is not understood at this point. Fluorescence microscopy subsequent to the experiment showed only modest staining of the *Pseudomonas* bacteria and much less for the *Staphylococcus*. This may have been due to residual free dye from the fluorescently labeled virus probe preparation. Additionally, if there is residual dye, it could stain free nucleic acid or small cellular debris remaining from the phage isolation. Another explanation is that there are effects from non-optimized phage/host ratio and media.

FIG. 8 shows the response of an MS2/fluorescently labeled virus probe prepared with YOPRO to two strains of *E. coli* and to *E. faecalis*. There is a clear difference in the response to the two strains.

Another example of host specificity is shown in FIG. 9, where the fluorescence intensity from a P1/fluorescently labeled virus probe and its host, *Vibrio natriegens* (Vn), is presented with the signals from non-host bacteria. Non-specific effects have been observed with *Bacillus* in several experiments conducted prior to studies of ionic strength effects, but it is not always reproducible, as the experiments with T4 in FIGS. 10a and 10b show. Previous work conducted and repeated here showed that *B. subtilis* has an unusually high affinity for many nucleic acid fluorophores, and for SYTOX in particular, as summarized in Table 5.

In Table 5, the percent increase in fluorescence signal is shown for two fluorophores and several bacteria, and the high signal from *B. subtilis* is quite striking. It is possible that at higher bacteria concentrations, which were used for many of these preliminary specificity experiments (e.g., 10E7 cells/ml) that phage and bacteria (host and non-host) compete for the fluorophore and that there may be some exchange of fluorophore from the phage to the bacteria. It is very likely, however, that fluorophores will exhibit different binding constants to the phage.

TABLE 5

Preferential Staining of *B. subtilis* by DNA Fluorophores
% Increase in Fluorescence upon Staining Bacterial
Nucleic Acid (no phage present)

| Fluorophore | Bacteria | | | |
|---|---|---|---|---|
| | Pa | Bs | Ec | Ef |
| YOPRO | 3740 | 7429 | 966 | 157 |
| SYTOX | 14664 | 39691 | 3103 | 394 |

Subsequent testing conducted with VD stained with SYTOX showed the characteristic "halo" of phage around the host *E. faecalis* in both a solution phase test and on a sensor surface, with only minimal cross-reactivity observed.

Quantitative Response and Sensitivity

As described above, the fluorescently labeled virus probes could be fabricated for several target bacteria and potential pathogens. Selectivity and rapid response are two very important characteristics of the assay of the present invention that are required for testing the safety of potable water supplied. Quantitative response and wide dynamic sensing range are less important, as long as the assay can function as a threshold sensor. However, preliminary experiments have determined both the sensitivity and quantitative response.

FIG. 11a shows the response of P1/fluorescently labeled virus probe to its host *V. nalriegens* as a function of bacteria concentration. The corresponding calibration curve derived from those data is shown in FIG. 11b, and shows a good correlation with exponential behavior.

FIG. 12 shows the response of P1/fluorescently labeled virus probes to host cells over an extended concentration range. Bacteria concentrations were plotted as cells/ml, but correcting for the sample size (100 µl), the actual number of cells is one order of magnitude lower (i.e., 10E3 cells-10E7 cells).

The digital images corresponding to these samples are shown in FIG. 13. As the cell concentration increases, more phage attach to the cells, due in part to increased collision frequency. The greater number of fluorescently labeled virus probe/host complexes is clear from images in FIG. 13. In FIG. 13, A-F corresponds to the concentrations 10E4-10E8 per mL. In 13A, several individual fluorescently labeled virus probes are evident. In FIG. 13B, a single bright fluorescently labeled virus probe/host complex is seen with the characteristic "halo" of phage. In FIG. 13F, numerous fluorescently labeled virus probe/host complexes can be seen.

As an added check that the fluorescently labeled virus probes were indeed associating with the bacteria, a direct count was made of the fluorescently labeled virus probes alone in the supernatant, isolated from the original fluorescently labeled virus probe/bacteria mixture using SYBR Green I. These results are shown in Table 6.

TABLE 6

Direct Count of FLVP/Host Complexes Original Concentration
of FLVP was 2.1E8 before mixing in reaction mixture

| Sample | Counts |
|---|---|
| Control | 2.80E+07 |
| 7.50E+04 | 2.60E+07 |
| 7.50E+05 | 1.70E+07 |
| 7.50E+06 | 1.40E+07 |
| 7.50E+07 | 5.80E+06 |
| 7.50E+08 | 3.90E+06 |

As was expected, the number of phage in the supernatant decreases as the concentration of host in the sample increases. This result should be regarded as a non-optimized response. Although the fluorescence signal did not increase at cell concentrations of 10E3, several phage/host complexes were observed, as shown in FIG. 13b. When integrated with a CCD detection system, it will be possible to detect even very small numbers of bacteria.

A similar experiment with non-host bacteria was performed with some-interesting results. FIG. 14 shows P1/fluorescently labeled virus probe response to *E. coli* as a function of bacteria concentration. Correcting for sample size the number of organisms in the sample ranges from 10E3-10E7. There was no change in fluorescence intensity until a high concentration was tested, about 10E9. Microscopic examination bore this out, in that the stained cells were not observed until the highest concentration of cells was added. There was also a fundamental difference in appearance, in that the cells look as if they are directly stained with fluorophore, and did not exhibit the characteristic fluorescently labeled virus probe "halo."

The fluorescently labeled virus probe concentration in the supernatant was determined as for the previous experiment using SYBR Green I direct count. The phage counts did not increase from the control level (~1E8) as the bacteria concentration increased. It should be noted that a good phage count could not be obtained at the highest bacteria concentration because there were too many residual bacterial cells on the membrane.

To verify the presence of bacteria at the center of the fluorescently labeled virus probe/host complexes, the sample was counterstained with DAPI. The fluorescence images at two different wavelengths (corresponding to the SYTOX emission wavelength and the DAPI emission wavelength) were compared and are shown in FIGS. 15a and 15b. The DAPI images show very brightly stained bacteria at the center of the complex. Much more distinct phage/host complexation and the characteristic "halo" of phage surrounding the bacteria was seen in most cases after the samples were prepared in solutions of higher ionic strength rather than deionized water. The optimum ionic strength of a solution for detecting a particular bacterium is preferably that of the media in which the virus is found naturally, e.g., fresh water, seawater, blood, milk, and the like.

Fluorescently Labeled Virus Probe Concentration

A single experiment was conducted to study the effect of fluorescently labeled virus probe concentration on phage/host interaction in the presence of a fixed concentration of bacteria. The fluorescently labeled virus probe concentration ranged from 1E4 to 1E8 pfu/ml, and the bacteria were present at 1E8 cells/ml. After incubation, the sample was filtered onto a 0.2 micron membrane and studied using fluorescence microscopy. Stained complexes were seen at all fluorescently labeled virus probe concentrations, but the number of complexes did not seem to increase with increasing fluorescently labeled virus probe concentration.

Response Time

Real-time experiments were conducted using an epi-fluorescence microscope interfaced with a CCD camera. A small aliquot of stained bacteria were deposited onto a microscope slide and brought into focus using a 10× objective (where the focus is less critical). This slide was replaced with an identical slide and E. coli sample, with the cells unstained. The CCD camera began acquiring images, and an aliquot of T4/fluorescently labeled virus probe was added to the slide. The response time in solution was estimated to be less than one minute, based on the time required to see the first fluorescently labeled virus probe/host complexes.

FIG. 16 shows an example of this image. More complexes formed over the next several minutes. This observation is consistent with qualitative observations that the phage/host interaction is very rapid.

Preliminary Interferent Testing

Residual dye can be observed under the microscope; it can be observed via its interaction with bacteria; it can be checked for using DNA or RNA standard solutions.

Demonstration of FLVP Selectivity in Mixtures of Host and Non-Host Bacteria

FLVP's were prepared using the P1 phage stained with SYTOX. The P1 FLVP's were tested in solution using host $V.$ $natriegens$ bacteria, a mixture of $V.$ $natriegens$ (Vn), $E.$ $coli$ (Ec), and $E.$ $faecalis$ (Ef), and a mixture of non-host Ec and Ef. The concentration of each bacterium was 3.0E5 cells/mL. After the mixture was incubated for 15 minutes, the mixture was filtered through 0.2 microns filter membrane, the number of cells were counted by counting the number of FLVP/bacteria complexes, and the results are summarized in Table 7.

TABLE 7

|  | Vn (host alone) | Vn, Fc, Ef | Ec, Ef (non-host mix) |
|---|---|---|---|
| # Bacteria in Sample | 3E5 cells/mL | 3E5 cells/mL | 3E5 cells/mL |
| # FLVP/bacteria complexes counted | 3E5 cells/mL | 2.8E5 cells/mL | none observed |

In the host alone sample, the results were quantitative with the number of complexes counted, corresponding to the number of host bacteria added. The same was true for the mixture, with the number of complexes counted close to the number of host cells present in the sample. No FLVP bacteria complexes were observed in the non-host mixture of $E.$ $coli$ and $E.$ $faecalis.$ Demonstration of FLVP Biosensor and Detection in Mixtures FLVP sensors were prepared using BC1 phage (selective for $B.$ $cereus$) stained with SYTOX and immobilized on an agarose polymer membrane. Sensors were prepared with different numbers of FLVP (i.e., 50 microliters or 100 microliters). A mixture of host and non-host cells (1E8 cells/mL starting concentration) was prepared using $B.$ $cereus$ (Bc), *B. subtilis* (Bs), and *E. coli* (Ec). Three microliter samples were added to the sensor consisting of host alone, (i.e., *B. Cereus*, the mixture of three bacteria, or the non-host cells as a control). The number of cells introduced to the sensor therefore was 3E5 cells.

Fluorescence microscopy and direct counting was used to determine the number of FLVP/host pairs and the results are summarized in the Table 8 below.

TABLE 8

| Amount of phage immobilized | Host only (Bc) | Mixed culture (Bc, Bs, Ec) | Mixed culture (Bs, Ec) |
|---|---|---|---|
| 50 uL | $2.8 \times 10^5$ | $1.9 \times 10^5$ | 0* |
| 100 uL | $2.1 \times 10^5$ | $2.9 \times 10^5$ | 0* |

*few stained cells were found but none with the characteristic halo formation

Only on the sensors exposed to host only (Figure A) and to the mixture of host and non-host cells (Figure B) were FLVP/host pairs observed and exhibited the characteristic "halo". The results were also nearly quantitative for two different numbers of immobilized phage. The sensors exposed to the mixture of non-host cells showed no FLVP/host pairs and only a few stained cells (Figure C).

Demonstration of a FLVP Biosensor in Tap Water and Skim Milk

FLVP biosensors were prepared on agarose membranes using BC1 phage for *Bacillus cereus* (a food pathogen). Skim milk and tap water samples were spiked with either (not a mixture) 1.4E8 *B. cereus* cells (the target) or 2.9E8 *V. natriegens* bacteria. The sensors were examined under the microscope. A 3 microliter sample volume was added to the FLVP sensor surface (corresponding to ~4E5 cells *B. cereus* and 9E5 cells *V. natriegens*). The sensors were examined under the fluorescence microscope and direct counting used to enumerate the number of cells with the characteristic phage "halo".

The results summarized below in Table 10 show that only the samples with host *B. cereus* had the phage "halo" and the results were quantitative. That is the number of cells counted was very close to the number of target cells in the sample. For *V. natriegens* some stained cells were observed but no phage "halos".

TABLE 10

| Skim milk | Control | *B. cerus* | *V. natriegens* |
|---|---|---|---|
| Calculated # of cells | 0 | $4.2 \times 10^5$ | $8.7 \times 10^5$ |
| # of cells counted | 0 | $3.0 \times 10^5$ | Stained cells, no count |

The FLVP/*B. cereus* complexes are shown in Figure A below, compared to a control (no cells, Figure B) and the non-host, *V. natriegens*, sample (Figure C).

Residual Dye

Residual fluorophore can confuse the fluorescence intensity measurements and microscope investigations. Fluorescently labeled virus probes were prepared by incubating the fluorophore with the bacteriophage for 48-72 hours. After filtration, some dye was retained on the bacteriophage. This dye is only weakly bound to the phage and can leach into the surrounding media, thereby causing a high background signal, or directly staining the bacterial targets (host and non-host).

A reliable protocol was established to clean up the fluorescently labeled virus probe preparation after incubation with the fluorophore. A centrifugal concentrator with a molecular weight cutoff of 50K was used to separate the phage from the dye solution after three successive wash stages. The four filtrates were tested after each separation for the presence of residual dye by adding 2.5E8 cells/ml of *Bacillus subtilis* indicator cells. Any residual dye would brightly stain the cells. These samples were then examined using fluorescence microscopy to determine the number of stained cells present, and, indirectly the amount of residual dye. As shown in FIG. 17, the signal due to stained cells falls off quickly with each successive wash stage. The inset presents the same data with the control subtracted. The microscope images of the third and fourth filtrates reveal very few and faintly stained cells.

Another assay protocol was developed using standard DNA solutions to test for residual dye. This method eliminates any biological variability affecting the degree of staining, such as age or physiological states of the cells. The DNA standard concentration was optimized for detection of low residual dye concentrations, and was determined to be 25 µg/ml. Calibration curves for SYTOX, YOPRO, and YOYO are presented in FIG. 18. The inset shows the response in the lower concentration ranges. A lower detection limit of 1.4 nM for SYTOX and 2.4 nM for YOPRO and YOYO was calculated based on the results in FIG. 18.

The DNA assay was used to detect the residual dye in a T4 FLVP preparation, stained with YOPRO, and these results are shown in FIG. 19. Although a large amount of dye had been removed after the first wash step (filtrate #2), there was little or no residual dye after the third wash (filtrate #4).

FVLP Response in Mixed Cell Population

One of the distinguishing characteristics of the assay of the present invention is the potential for high discrimination capability in solutions containing both target and non-target organisms. To demonstrate this potential, experiments were conducted using six different fluorescently labeled virus probes: T4/SYTOX, T4/YOPRO, MS2/SYTOX, MS2/YOPRO, P1/SYTOX, and P1/YOPRO. The cell lines included host and non-host organisms: *E. coli, E. faecalis, V. natriegens*, and *Actinobacter*. The experiments were conducted in a media containing counter ions similar to artificial seawater containing, $Ca^{2+}$, $Mg^{2+}$, $Na^{1+}$, $K^{1+}$. The cell concentrations as $2.5 \times 10^5$ cells/ml. The controls included fluorescently labeled virus probe alone, fluorescently labeled virus probe plus host, and fluorescently labeled virus probes plus a mixture of non-host organisms. There was modest (~1%) non-specific staining with T4 and MS2.

The P1/fluorescently labeled virus probe results were much cleaner and are summarized in Table 9. The control containing fluorescently labeled virus probe plus host showed the characteristic fluorescently labeled virus probes "halo" around the unstained cells. In the P1/non-host control, no stained cells were obtained. In the P1/mixture sample, unstained cells with the fluorescently labeled virus probe "halo" were observed. Although the identity of the bacteria at the core of the complex was undetermined, when these clusters were counted the number corresponded well with the number of host organisms in the sample. These results indicate there is good support for selectivity of the test in mixed bacterial populations.

TABLE 9

Summary of Mixed Cell Population Experiments with P1/FLVP

| Sample | Observation |
| --- | --- |
| P1 | Phage observed |
| P1/host | Phage/host clusters observed |
| P1/non-host | No cells stained |
| P1/mixture | Phage/host clusters observed* |

*Direct count of stained clusters corresponds to number of host cells in the sample A digital image from the fluorescence microscope studies is shown in FIG. 20. FIG. 20a shows P1 fluorescently labeled virus probes in a mixture of non-host bacteria. FIG. 20b shows fluorescently labeled virus probe/cell complexes in a mixture containing host and non-host cells.

Demonstration of an FLVP Biosensor

To prepare a biosensor, the fluorescently labeled virus probes are immobilized on an optical substrate such as a quartz window or an optical fiber. Alternatively, a very low volume of the sample solution could be immobilized, and the fluorescently labeled virus probes introduced as reporter molecules. It is preferable to immobilize the molecular recognition element. Polymers for this can include agarose, polyvinyl pyrrolidone (PVP), and polylysine. PVP and agarose are preferred, because they give a low background and are easily prepared into a homogeneous film. Polylysine films are good surfaces for bacteria based on electrostatic interactions. However, other polymers having these characteristics could also be used for this purpose. Sensors were prepared on glass coupons. One hundred µl of each polymer solution (e.g., 1% PVP) was spread onto the coupon and dried overnight. Fluorescently labeled virus probes were prepared using T4 and either YOPRO or SYTOX. 50 µl of fluorescently labeled virus probe solution was added to the film and allowed to soak into the polymer membrane and dry for four hours. 2 microliters of *E. coli* suspension in 0.5% NaCl was added to the sensor surface and protected with a cover slip. After incubating for 30 minutes, the sensor surface was examined under the fluorescence microscope.

The results are shown in FIG. 21. FIG. 21a shows T4 phage stained with YOPRO and immobilized in the PVP polymer membrane. The fluorescently labeled virus probe controls are in FIG. 21a. FIGS. 21b and 21c show phage/host complexes, using T4/SYTOX probe. Similar results were obtained for the agarose films.

Biosensor films were also prepared using P1/fluorescently labeled virus probe immobilized in PVP and agarose. The results are shown in FIGS. 22 and 23.

FIGS. 22a and b are digital microscope images of the fluorescent phage/host complexes. FIG. 22a shows fluorescently labeled virus probe/host complexes on an agarose membrane. FIG. 22b shows fluorescently labeled virus probe/host complexes on a PVP membrane.

In FIG. 23, the fluorescence signal from the biosensor was measured using a double monochromator system, as shown in FIG. 6. The fluorescence intensity increased appreciably, 255% and 313%, over the control when the fluorescently labeled virus probe complex forms.

It is noteworthy that the solid-phase biosensor of the present invention does not require addition of reagents or other manipulation, making it easy to use to obtain rapid detection of pathogens without the requirement for specialized training of the operator.

The present invention thus provides virus probes for rapid, selective detection of bacteria, with good sensitivity and dynamic range. The present invention has verified fluorescently labeled virus probes response in a solid-phase biosensor, although a liquid phase biosensor could also be used. The system of the present invention provides good results even with mixed bacterial populations.

The biosensors of the present invention are an important simple tool for real-time warning and protection of water supplies, and minimize time and logistic burdens associated with conventional microbiological analysis.

Matrices of phage/host pairs can readily be screened for maximum specificity using a combinatorial approach. This can be effected by one skilled in the art without undue experimentation.

An alternative embodiment of the present invention is a flow cell that introduces a flow stream to the biosensor elements to allow direct optical interrogation of the sensor surface. This cell is designed so that it can be placed in line, or in a slipstream, for example in a water reclamation testbed.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

REFERENCES

Hennes, K. P., and Suttle, C. A., "Direct counts of viruses in natural waters and laboratory cultures by epifluorescence microscopy," *Limnol. Oceanogr.*, 40, 1050-1055 (1995).

Hennes, K. P., Suttle, C. A., and Chan, A. M., "Fluorescently Labeled Virus Probes Show that Natural Virus Populations Can Control the Structure of Marine Microbial Communities," *Appl. Environ. Microbiol.*, 61, 3623-3627 (1995).

Holland, R. D., Duffy, C. R., Rafii, F., Sutherland, J. B., Heinze, T. M., Holder, C. L., Voorhees, K. J., and Lay Jr, J. O., "Identification of Bacterial Proteins Observed in MALDI-TOF Mass Spectra from Whole Cells," *Anal. Chem.*, ASAP Article, 10.1021, Jun. 16, 1999.

Winkler, M. A., Uher, J., and Cepa, S., "Direct Analysis and Identification of *Helicobacter* and *Campylobacter* Species by MALDI-TOF Mass Spectrometry," *Anal. Chem.*, ASAP Article 10.1021, Jul. 2, 1999.

Arnold, R. J., Karty, J. A., Ellington, A. D., and Reilly, J. P., "Monitoring the Growth of a Bacteria Culture by MALDI-MS of Whole Cells," *Anal. Chem.*, 71, 1990-1996 (1999).

Belgrade, P., Benett, W., Hadley, D., Richards, J., Stratton, P., Mariella, R., and Milanovich, F., "PCR Detection of Bacteria in Seven Minutes," *Science*, 284, 449-450 (1999).

Paddle, B., "Biosensors for chemical and biological agents of defense interest," *Biosensors & Bioelectronics*, 11, 1079-1113 (1996).

Cao, K. L., Anderson, G. P., Ligler, F. S., and Ezzel, J., "Detection of *Yersinia pestis* Fraction 1 antigen with a fiber optic biosensor," *J. Clin. Microbiol.*, 33, 336-341 (1995).

Wadkins, R. M., Golden, J. P., Pritsiolas, L. M., and Ligler, F. S., "Detection of multiple toxic agents using a planar array immunosensor," *Biosensors & Bioelectronics*, 13, 407-415 (1998).

Stahl, D. "Development of DNA Microarrays for the Rapid identification of Novel microbial Agents in Biologically Complex Settings," presentation to the Biological Agent Detection and Identification Program Overview, DARPA Biological Warfare Defense Program, Defense Sciences Office, Apr. 27-30, 1999 Santa Fe, N. Mex.

Brewster, J. D., Gehring, A. G., Mazenko, R. S., VanHouten, L. J., and Crawford, C. J., "Immunoelectrochemical Assays for Bacteria: Use of Epifluorescence Microscopy and Rapid-Scan Electrochemical Techniques in Development of an Assay for Salmonella," *Anal. Chem.*, 68, 4153-4159 (1996).

Brown, C. W., Li, Y., Seelenbinder, J. A., Pivarnik, P., Rand, A. G., Letcher, S. V., Gregory, O. J., and Platek, M. J., "Immunoassays Based on Surface-Enhanced Infrared Absorption Spectroscopy," *Anal. Chem.*, 70, 2991-2996 (1998).

Goodridge, L., Chen, J., and Griffiths, M., "Development and Characterization of a Fluorescent-Bacteriophage Assay for Detection of *Escherichia coli* 0157:H7," *Appl. Environ. Microbiol.*, 65, 1397-1404 (1999).

Potyrailo, R. A., Conrad, R. C., Ellington, A. D. and Hieftje, G. M., "Adapting Selected Nucleic Acid Ligands (Aptamers) to Biosensors," *Anal. Chem.*, 70, 3419-3425 (1998).

German, I., Buchanan, D. D., and Kennedy, R. T., "Aptamers as Ligands in Affinity Probe Capillary Electrophoresis," *Anal. Chem.*, 70, 4540-4545 (1998).

P. F. Kemp et. al. (eds), *Current Methods in Aquatic Microbial Ecology*, Chapter 15, pp. 121-134, Lewis Publs, Boca Raton, Fla. (1993).

What is claimed is:

1. A biosensor for detecting bacteria comprising: a probe comprising a fluorescently labeled virus, wherein the probe is immobilized on a substrate, and wherein the substrate is selected from the group consisting of a quartz window, an optical fiber, an optical waveguide glass, a sol-gel, and a polymeric film; and an optoelectronic interface capable of detecting a probe-host bacterium complex, wherein the biosensor is a solid-phase biosensor, and wherein the virus is BC1 and the fluorescent label is SYTOX or the virus is T4 and the fluorescent label is SYTOX.

2. The biosensor of claim 1, further comprising a data acquisition system.

3. The biosensor of claim 1, wherein the probe is part of a flow cell.

4. The biosensor of claim 1, wherein the substrate is a polymeric film comprising a polymer selected from the group consisting of agarose, polyvinyl pyrrolidone, dextran, gelatin, polyvinylalcohol and polylysine.

5. The biosensor of claim 1, wherein the probe is a flow cell that is in line with a flowing fluid.

6. The biosensor of claim 1, wherein the probe is semi-selective.

7. The biosensor of claim 1, wherein the bacteria is *E. coli*, *E. faecalis*, *E. herbicola*, an Enterococci, Streptococci, Bacteroides, Bifidabacterium, Legionella, Yersinia, Tularemia, Pseudomonas, *P. aeruginosa*, Staphylococcus, *S. aureus*, Bacillus, *B. subtilis*, Acinetobacter sp., *V. natriegens*, *B. cereus*, or a combination 'thereof.

8. The biosensor of claim 1, wherein the biosensor is from 0.8 to 5 mm in size.

9. The biosensor of claim 1, wherein the biosensor detects a plurality of pathogens.

10. The biosensor of claim 1, wherein the biosensor detects many species and strains of a pathogen.

11. The biosensor of claim 1, wherein a probe is provided in a sensor array.

12. The biosensor of claim 11, wherein the sensor array comprises redundant sensors.

13. The biosensor of claim 1, wherein the probe-host bacterium complex is detected by wavelength-specific fluorescence spectroscopy.

14. The biosensor of claim 1, wherein the virus is BC1 and the fluorescent label is SYTOX.

15. The biosensor of claim 1, wherein the virus is T4 and the fluorescent label is SYTOX.

* * * * *